United States Patent [19]

Moore

[11] Plant 4,680

[45] Mar. 31, 1981

[54] MINIATURE ROSE PLANT

[76] Inventor: Ralph S. Moore, 2519 E. Noble Ave., Visalia, Calif. 93277

[21] Appl. No.: 115,743

[22] Filed: Jan. 28, 1980

[51] Int. Cl.[3] ..... A01H 5/00

[52] U.S. Cl. ..... Plt./10

[58] Field of Search ..... Plt./10

[56] References Cited

U.S. PATENT DOCUMENTS

P.P. 4,512 3/1980 Moore ..... Plt./10

*Primary Examiner*—James R. Feyrer

[57] ABSTRACT

The subject of the present disclosure is a new and distinct variety of miniature rose plant characterized by the deep red color of the buds and flowers and by the profusion of bloom.

1 Drawing Figure

1

The present invention relates to a new and distinct variety of hardy, dwarf, bush type rose plant of the miniature class; the variety being primarily characterized—as to novelty—by deep red buds and flowers which in general color effect are similar to Little Curt (miniature—not patented).

The variety is further characterized by:

An abundance of bloom, with flowers, on mature plant, usually borne several to the stem in loose clusters.

Little or no fragrance.

A plant which is vigorous, of rounded somewhat upright shape with semi-glossy to matt, small foliage with pointed leaflets; the buds and flowers being similar in form and size to Sheri Anne (miniature—U.S. Plant Pat. No. 3,826).

The plant, which has a normal height of 14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Fairy Moss (miniature—U.S. Plant Pat. No. 3,083) as the seed parent and Fire Princess (miniature—U.S. Plant Pat. No. 3,084), as the pollen parent.

Subsequent to origination of the variety I successfully reproduced it, at Sequoia Nursery located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*International identification.*—Variety: Morgal. Commercial synonym: Galaxy

2

Flowers borne: Usually several together in clusters of 3–5 or more (sometimes singly) on slender wirey stems.

Quantity of bloom: Abundant both outside and in greenhouse.

Bud:

*Peduncle.*—Medium to long; slender but sturdy; erect; medium green, sometimes tinted bronze (outdoors); Hairs — few — very short.

*Before calyx breaks.*—Size — small. Form long; pointed with several foliaceous apendages and numerous very small hairs on surface of bud; with foliaceous parts extending beyond the tip of the bud equal to one-half or more of its length. Color — medium green, occasionally tinted with bronze (outdoors).

*As calyx breaks.*—Color — deep red — near Maroon 1030, sometimes lighter red near base with white area at base. Opening: opens well in all weather.

Bloom:

*Size when fully open.*—Small, averaging about 35–40 mm (1½").

*Petalage.*—Double — averaging about 25 petals, arranged regularly plus sometimes several small petaloids.

*Form.*—Cupped at first, becoming more high in the center, then more open with petals reflexing loosely outward, and later at maturity, open and rolled loosely outward and downward. Open flowers show stamens.

Petals: Fairly thick; velvety on inside and satiny on outside surface.

*Shape.*—Outside petals, broad lanceolate (nearly round) with rounded tip; intermediate — broad lanceolate with rounded tip; inside — lanceolate with rounded tip.

Color: Newly opened flower from a plant grown in plastic greenhouse (October 1979), Visalia, Calif.

*Outside petals.*—Outside surface — near Indian Lake 826/2 with small pink area at base. Inside surface — near Indian Lake 826/1 or 826/2 with small white area at base.

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers — rich deep red. Three days open — color similar to newly opened flowers. Behavior — opens well in all weather. Color lasts better than most other red miniatures. Spent petals drop off. Flower longevity (May 1979) — plant in pot 7–14 days or longer. Cut flowers at living room temperature 4–7 days or longer.

Reproductive organs:

*Stamens.*—Abundant, arranged regularly about pistils.

*Filaments.*—Varying length, medium long, yellow.

*Anthers.*—Well formed; yellow.

*Pollen.*—Moderate amount.

*Pistils.*—Average number.

*Styles.*—Fairly even; medium to long length; bunched; color — whitish.

*Ovaries.*—All enclosed in calyx.

*Hips.*—None to few.

*Sepals.*—Permanent; spear shape; recurved against peduncle.

*Seed.*—Few or none.

Foliage:

*Leaves.*—Compound of five (sometimes three or seven) leaflets; fairly small; leathery; semi-glossy to matt.

*Leaflets.*—Shape: broad, nearly oval; apex acute; base rounded or rounded acute. Margin serrate. Color: medium to dark green; new growth — normal (medium) green. Rachis: medium strength; upper side may have a few tiny short prickles or hairs, grooved; underside sparsely thorny with few or no tiny prickles. Stipules: medium long to long; narrow to medium width; short length; narrow points which turn out usually at about 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Average; slender; hooked downward; color; brown. Prickles — none.

*Branches.*—Color: medium green. Thorns: moderate number; medium length; slender; inclined downward. Medium oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded to upright, much branched habit, substantially as illustrated and described, characterized by buds and flowers of a rich deep red color, being of a shade generally near Indian Lake 826/1 or 826/2, the bud and flower resembling the variety Sheri Anne (U.S. Plant Pat. No. 3,826) in form and size; and further characterized by a plant of vigorous and compact growth habit, easy to propagate from cuttings or by budding, with an abundance of small to medium size semi-glossy to matt foliage and an abundance of flowers borne usually in loose clusters of 3 to 5 or more.

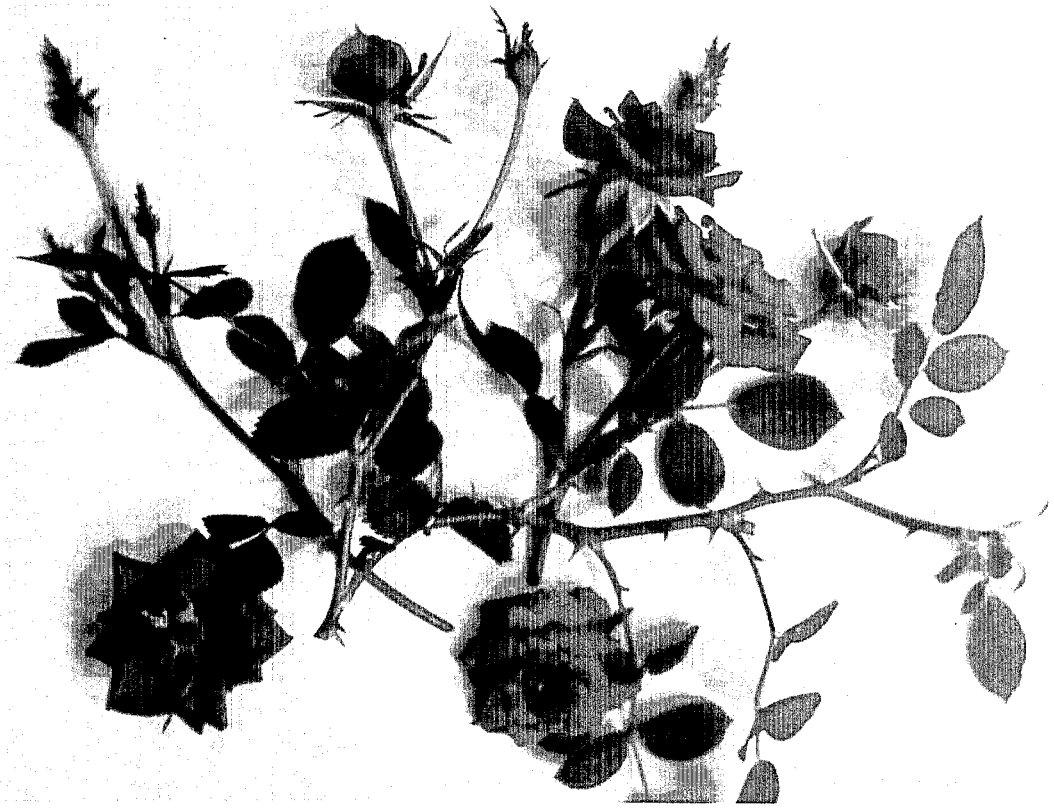

* * * * *